US008999065B2

(12) United States Patent
Kazachkin et al.

(10) Patent No.: US 8,999,065 B2
(45) Date of Patent: Apr. 7, 2015

(54) SUPERCRITICAL HYDROLYSIS OF BIOMASS

(71) Applicant: Renmatix, Inc., King of Prussia, PA (US)

(72) Inventors: Dmitry Vitalyevich Kazachkin, Bryn Mawr, PA (US); Manuk Colakyan, Ardmore, PA (US); Frederick John Moesler, Berwyn, PA (US)

(73) Assignee: Renmatix, Inc., King of Prussia, PA (US)

( * ) Notice: Subject to any disclaimer, the term of this patent is extended or adjusted under 35 U.S.C. 154(b) by 0 days.

(21) Appl. No.: 13/941,072

(22) Filed: Jul. 12, 2013

(65) Prior Publication Data
US 2014/0014092 A1 Jan. 16, 2014

Related U.S. Application Data

(60) Provisional application No. 61/671,264, filed on Jul. 13, 2012.

(51) Int. Cl.
C13K 1/02 (2006.01)
C13K 13/00 (2006.01)

(52) U.S. Cl.
CPC ............... *C13K 1/02* (2013.01); *C13K 13/002* (2013.01); *C13K 13/00* (2013.01)

(58) Field of Classification Search
None
See application file for complete search history.

(56) References Cited

U.S. PATENT DOCUMENTS

| | | | | |
|---|---|---|---|---|
| 7,901,663 B2 * | 3/2011 | Lenglet | ............... | 423/650 |
| 7,955,508 B2 * | 6/2011 | Allan et al. | ............... | 210/749 |
| 8,057,639 B2 | 11/2011 | Pschorn et al. | | |
| 2002/0172650 A1 | 11/2002 | Cannell et al. | | |
| 2007/0148750 A1 * | 6/2007 | Hoshino et al. | ............... | 435/161 |
| 2009/0221814 A1 | 9/2009 | Pschorn et al. | | |
| 2010/0069626 A1 | 3/2010 | Kilambi | | |
| 2010/0170504 A1 | 7/2010 | Zhang | | |
| 2011/0219679 A1 | 9/2011 | Budarin et al. | | |
| 2012/0108798 A1 | 5/2012 | Wenger et al. | | |
| 2012/0145094 A1 | 6/2012 | Simard | | |

FOREIGN PATENT DOCUMENTS

| | | |
|---|---|---|
| CN | 101787398 | 7/2010 |
| JP | 2001262162 | 9/2001 |
| JP | 2008248202 | 10/2008 |
| WO | 2011091044 | 7/2011 |
| WO | 2012060767 | 5/2012 |
| WO | 2013070160 | 5/2013 |

OTHER PUBLICATIONS

Zoulikha et al, A thermomechanical pretreatment to improve enzymatic hydrolysis of wheat straw, 2009, Récents Progrès en Génie des Procédés, Numéro 98.*

(Continued)

*Primary Examiner* — Melvin C Mayes
*Assistant Examiner* — Stefanie Cohen
(74) *Attorney, Agent, or Firm* — Travis B. Gasa; Ballard Spahr LLP

(57) ABSTRACT

Methods are disclosed for processing biomass by single-stage supercritical hydrolysis, wherein the biomass has been size reduced.

27 Claims, 2 Drawing Sheets

(56) References Cited

OTHER PUBLICATIONS

Demirbas, "Sub- and super-critical water depolymerization of biomass", Energy Sources, Part A: Recovery Utilization, and Environmental Effects, 32(12), 2010, 1100-1110.

Ehara et al., "Characterization of the lignin-derived products from wood as treated in supercritical water", Journal of Wood Science, vol. 48, No. 4, Aug. 2002, pp. 320-325.

Galkin et al., "Subcritical and supercritical water: a universal medium for chemical reactions", Russian Chemicals Reviews, 7491, 2005, 21-35.

Graczyk et al., "Explosion pulping of lignocellulosic materials. Effect of steam explosion on plant raw materials and their constituents.", Przeglad Papierniczy, 46(12), 1990, 413-418.

Jeoh, "Steam Explosion Pretreatment of Cotton Gin Waste for Fuel Ethanol Production", Thesis submitted to the Faculty of the Virginia Polytechnic Institute and State Univeristy, Dec. 1998, 1-153.

International Patent Application No. PCT/US2013/050333, "International Search Report and Written Opinion", mailed Oct. 15, 2013, 10 pages.

Sasaki et al., "Direct hydrolysis of cellulose to glucose using ultra-high temperature and pressure steam explosion", Carbohydrate Polymers 89, 2012, 298-301.

Sasaki et al., "Dissolution and Hydrolysis of Cellulose in Subcritical and Supercritical Water", Industrial & Engineering Chemistry Research, 39(8), 2000, 2883-2890.

Savage, "Organic chemical reactions in supercritical water", Chemical Reviews (Washington, D.C.), 99(2), 1999, 603-621.

Savage et al., "Reactions at supercritical conditions: applications and fundamentals", AIChE Journal, 41(7), 1995, 1723-78.

Wang et al., "Influence of steaming time during steam-explosion on the chemical composition, crystallinity and enzymatic hydrolysis of *Lespedeza* bicolor stalks", Beijing Linye Daxue Xuebao, 31(5), 2009, 121-125.

Wang et al., "Influence of steaming explosion time on the physic-chemical properties of cellulose from *Lespedeza* stalks (*Lespedeza crytobotrya*)", Bioresource Technology 100, 2009, 5288-5294.

\* cited by examiner

SUPERCRITICAL HYDROLYSIS OF BIOMASS

CROSS-REFERENCE TO RELATED APPLICATIONS

This patent application claims the benefit of U.S. Provisional Patent Application No. 61/671,264, filed Jul. 13, 2012, which is hereby incorporated by reference in its entirety.

FIELD OF THE INVENTION

The present invention generally relates to methods of processing biomass using supercritical hydrolysis. More particularly, it relates to methods of processing biomass using single-stage supercritical hydrolysis.

BACKGROUND OF THE INVENTION

There exist methods for converting lignocellulosic biomass into fermentable $C_5$ and $C_6$ sugars, including supercritical hydrolysis, acid hydrolysis, and enzymatic hydrolysis.

In acid hydrolysis, strong mineral acids like sulfuric or hydrochloric are used as solvents to convert cellulosic solids into liquid phase sugars. Current acid hydrolysis technologies suffer from technological flaws and economical drawbacks. Technically, acid processes using dilute acids require high temperatures and pressures that can cause manufacturing equipment to suffer from corrosion, and the removal of the acids requires large amounts of neutralizing agents. Acid processes using concentrated acids can operate at lower temperatures and pressures, but they require significant capital and operating expenses for the removal and recycling of the acid. Accordingly, dilute acid systems require significant operating expense for the maintenance and upkeep of the system components, while concentrated acid systems required significant capital expense for sophisticated acid recovery systems and special materials during construction. Acid purchasing itself is a significant cost to the system.

The basis of the technology is well known, although it is not practiced on a large scale today due to the inherent economic challenges. Some are pursuing acid hydrolysis focusing on concentrated acids and special recovery systems. Some of these acid technologies have the potential to somewhat address the operating cost concerns of this process by recovering ever increasing amounts of the used acid, however, these extensive recovery systems require significant capital outlays causing the resulting sugar to be uneconomical.

Enzymatic hydrolysis involves developing biological catalysts that can solubilize hemicellulose or cellulose inherent in lignocellulosic biomasses. While there have been advances in this field (it has been researched for several decades), the challenges are twofold: economics and feedstock flexibility. Enzymatic hydrolysis faces a different set of challenges currently in the marketplace. First, the cost of the enzymes themselves is high. Second, enzymatic operations also face the question of building their own enzyme production facility or paying for and organizing several shipments of enzymes each week—with either scenario requiring substantial investment in upstream capital expense. Third, enzymes can also take days to break down biomass, causing high capital expenses. While the enzymatic routes produce very little by-products, the hydrolysis rates are very slow, necessitating large reaction vessels and large quantities of expensive enzymes. Enzymes are also relatively inefficient at conversion, so, the biomass is usually pretreated by steam explosion, conventional or specialized milling techniques, or using digester technology. Lastly, enzymes may need to be optimized for different types of biomass—a process that can take a very long time, cost significant amounts of money, and have an uncertain outcome.

It would be desirable to develop processes that utilize all types of feedstocks, including switchgrass, corn stover and cobs, wheat straw, and softwoods, especially feedstocks that can be stable to autohydrolysis. It would also be desirable to develop supercritical hydrolysis processes that utilize only water at elevated temperatures and pressures to quickly breakdown cellulose, because they would use no significant consumables and could produce much of their own process energy. The methods and compositions of the present invention are directed toward these, as well as other, important ends.

SUMMARY OF THE INVENTION

In certain embodiments, the invention is directed to processes capable of utilizing biomasses that are not suitable for autohydrolysis because of lack of sufficient acid functionalities (such as, softwoods and some grasses) with the use of supercritical water, which provides an acidic environment for the hydrolysis to occur. By feeding a slurry of fine biomass particles (for example, less than about 500 microns) directly to a supercritical reactor in a one-step process, the supercritical water enables hydrolysis of both hemicelluloses and cellulose simultaneously.

In certain embodiments, the invention is directed to processes capable of utilizing biomasses without sufficient acid functionalities, where certain two-step processes may not be as efficient as desired because they will either take a long time to realize the autohydrolysis or acid needs to be added. The one-step processes of the invention eliminate the necessity of adding acids to the process. Conventional processes hydrolyze the hemicelluloses from biomasses with limited acid functionalities using acid additives. The one step processes of the invention are superior to these competitive processes since no acid additives are used and the processes have a small reactor footprint. Moreover, conventional two step biomass hydrolysis processes typically separate hydrolyzed sugars into two streams: a first step that results in a $C_5$ stream and a second step that results in a $C_6$ stream. The separation of $C_5$ and $C_6$ sugar streams allows each stream to be separately and efficiently transformed (e.g., fermented) into desired end products in one or more subsequent processes. Some organisms, enzymes, or processes cannot easily handle a mixture of both $C_5$ and $C_6$ sugars, such that this stream separation is necessary in many cases for efficient transformations to occur. However, when autohydrolysis does not occur to a sufficient degree in a first step, a substantial amount of $C_5$ sugars remain after the first "autohydrolysis" step, and the second hydrolysis step produces a single stream of monosaccharides comprising both $C_5$ and $C_6$ sugars. In such a situation, the first "autohydrolysis" step adds significant capital and operating expenditures, without effectively separating the $C_5$ sugar stream from the $C_6$ sugar stream. Thus, the methods of the invention are superior in such a situation, where mixed $C_5$ and $C_6$ sugar streams are tolerated, or even desired. Moreover, even in situations where autohydrolysis may occur to a sufficient extent to separate a substantial portion of $C_5$ sugars from $C_6$ sugars, the methods of the invention are still desirable and beneficial for processes or transformations that can tolerate mixed $C_5$ and $C_6$ sugar streams, since the capital and operating expenditures for an autohydrolysis system can be avoided.

In one embodiment, the invention is directed to methods, comprising:
   size reducing a starting lignocellulosic biomass to form a lignocellulosic biomass having a particle size less than about 500 µm;
   forming a mixture comprising:
      water; and
      said lignocellulosic biomass having a particle size less than about 500 µm; and
   contacting water at a temperature of at least about 374° C. and a pressure of at least about 221 bar with said mixture for a duration sufficient to produce at least one $C_5$ or $C_6$ saccharide;
   wherein said mixture is substantially free of exogenous acid.

In one embodiment, the size reducing comprises steam exploding said starting lignocellulosic biomass optionally in the presence of a chemical selected from the group consisting of ammonia, sulfur dioxide, and mixtures thereof. In one embodiment, the size reducing comprises comminuting said starting lignocellulosic biomass.

In another embodiment, the invention is directed to products produced by the method.

In other embodiments, the invention is directed to compositions, comprising:
   about 0.1% by weight to about 4% by weight, based on the total weight of the composition, of $C_5$ monosaccharide;
   about 0.1% by weight to about 4% by weight, based on the total weight of the composition, of $C_5$ oligosaccharide having a degree of polymerization less than about 15;
   about 0.1% by weight to about 8% by weight, based on the total weight of the composition, of $C_6$ monosaccharide; and
   about 0.1% by weight to about 8% by weight, based on the total weight of the composition, of $C_6$ oligosaccharide having a degree of polymerization less than about 15.

In other embodiments, the invention is directed to compositions, comprising:
   about 0.1% by weight to about 4% by weight, based on the total weight of the composition, of $C_5$ monosaccharide; and
   about 0.1% by weight to about 8% by weight, based on the total weight of the composition, of $C_6$ monosaccharide.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
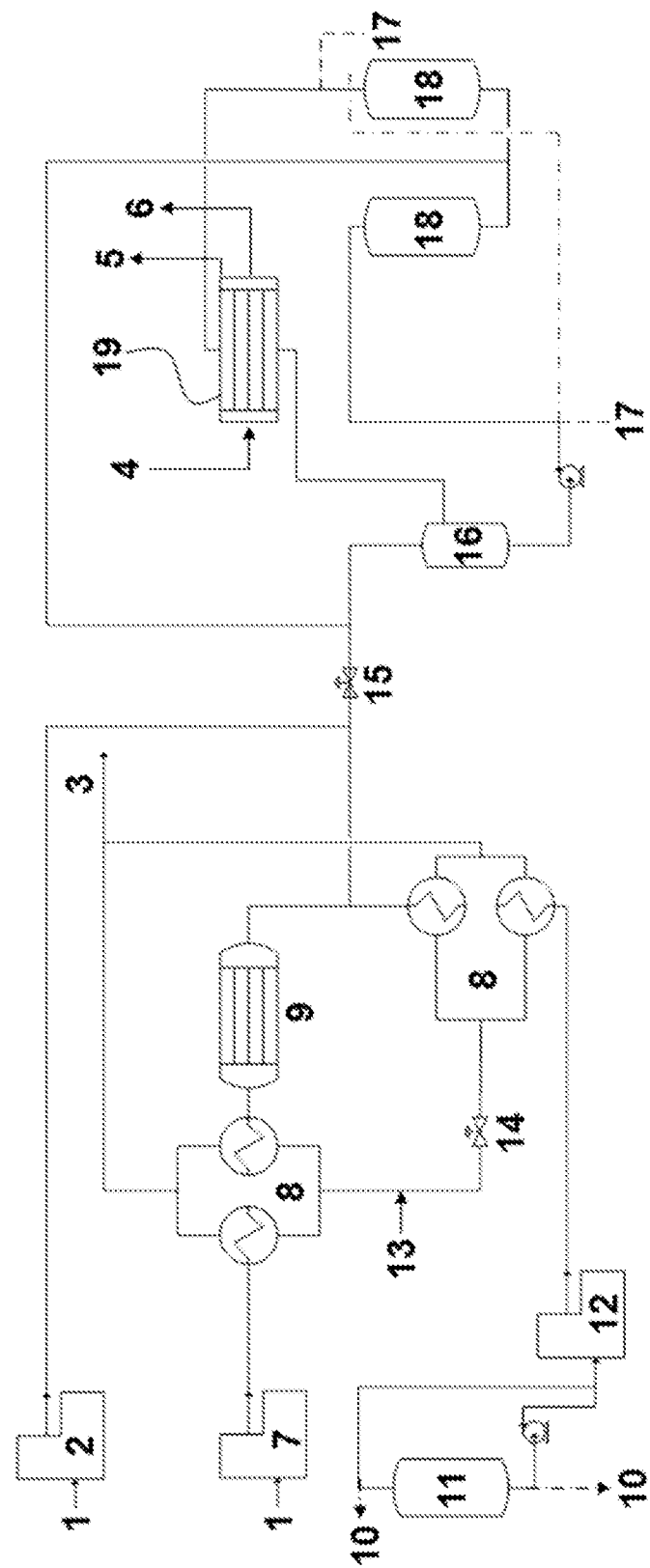
FIG. 1 is a schematic diagram of a supercritical hydrolysis system.

As employed above and throughout the disclosure, the following terms, unless otherwise indicated, shall be understood to have the following meanings.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near-critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. (preferably, at least about 100° C., and most preferably at least about 150° C.) but less than subcritical and at pressures such that water is in a liquid state As used herein, a fluid which is "supercritical" (e.g., supercritical water, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g., water and ethanol, water and $CO_2$, etc.). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, "continuous" indicates a process which is uninterrupted for its duration, or interrupted, paused or suspended only momentarily relative to the duration of the process. Treatment of biomass is "continuous" when biomass is fed into the apparatus without interruption or without a substantial interruption, or processing of said biomass is not done in a batch process.

As used herein, "resides" indicates the length of time which a given portion or bolus of material is within a reaction zone or reactor vessel. The "residence time," as used herein, including the examples and data, are reported at ambient conditions and are not necessarily actual time elapsed.

As used herein, the term "substantially free of" refers to a composition having less than about 1% by weight, preferably less than about 0.5% by weight, and more preferably less than about 0.1% by weight, based on the total weight of the composition, of the stated material.

As used herein, "$C_1$-$C_5$ alcohol" indicates an alcohol comprising 1 to 5 carbon atoms. Examples of $C_1$-$C_5$ alcohols include, but are not limited to, methanol, ethanol, n-propanol, isopropanol, n-butanol, s-butanol, t-butanol, i-butanol, n-pentanol, 2-pentanol, 3-pentanol, 2-methyl-1-butanol, 2-methyl-2-butanol, 3-methyl-1-butanol, 3-methyl-2-butanol, and 2,2-dimethyl-1-propanol. Mixtures of one or more of these alcohols may be used.

As used herein, "lignocellulosic biomass" refers to plant biomass containing cellulose, hemicellulose, and lignin from a variety of sources, including, without limitation (1) agricultural residues (including corn stover, sugarcane bagasse, rice hulls, oat hulls, and the like), (2) dedicated energy crops, (3) wood residues (including sawmill and paper mill discards), and (4) municipal waste.

As used herein with respect to biomass, "steam exploding" means a thermomechanochemical process used to breakdown the structural components of the biomass aided by heat in the form of steam (thermo), shear forces due to the expansion of moisture (mechano), and hydrolysis of glycosidic bonds (chemical). In the reactor, steam under high pressure penetrates the lignocellulosic structures due to a pressure differential, or by convection or diffusion. The steam may also simply heat water already present within the interstitial spaces of the biomass itself, thereby forming hot water and/or steam in the interstitial spaces. In the case of steam, the steam condenses under the high pressure, thereby "wetting" the material (in the case of hot water, the material will already be "wetted"). The water in the biomass hydrolyzes the acid functionalities of the hemicellulose, forming free organic acids, such as acetic acid. Acid byproducts may also form, such as formic acid. The acids, in turn, catalyze the depolymerization of hemicellulose, releasing xylo-oligosaccharides and limited amounts of gluco-oligosaccharides. Under extreme conditions, the amorphous regions of cellulose may be hydrolyzed to some degree. Excessive conditions, i.e., high temperatures and pressures, however, can also promote the degradation of xylose to furfural and glucose to 5-hydroxymethyl furfural. The "wet" biomass is "exploded" when the pressure within the reactor is released. Several phenomena occur at this point. First, the condensed moisture within the structure evaporates instantaneously due to the sudden decrease in pressure. The expansion of the water vapor exerts a shear force on the surrounding structure. If this shear force is high enough, the vapor will cause the mechanical breakdown of the lignocellulosic structures.

As used herein, "comminuting" means any mechanical technique for the size reduction of a solid, such as crushing, grinding, collision milling, and the like.

Accordingly, in one embodiment, the invention is directed to methods, comprising:
  size reducing a starting lignocellulosic biomass to form a lignocellulosic biomass having a particle size less than about 500 µm;
  forming a mixture comprising:
    water; and
    said lignocellulosic biomass having a particle size less than about 500 µm; and
  contacting water at a temperature of at least about 374° C. and a pressure of at least about 221 bar with said mixture for a duration sufficient to produce at least one $C_5$ or $C_6$ saccharide;
  wherein said mixture is substantially free of exogenous acid.

In certain embodiments, the size reducing comprises steam exploding said starting lignocellulosic biomass optionally in the presence of a chemical selected from the group consisting of ammonia, sulfur dioxide, and combinations thereof. In certain other embodiments, the size reducing comprises comminuting said starting lignocellulosic biomass.

FIG. 1 illustrates an example of a system that can be used to carry out a method of the invention. The features of FIG. 1 include water (1), quench pump (2), condensate (3), cooling water supply (4), exhaust to roof (5), cooling water return (6), supercritical water pump (7), steam heaters (8), electric heaters (9), water return (10), cellulose hydrolysis feed tank (11) (i.e., a tank holding a mixture of biomass and water that is subsequently fed into the supercritical hydrolysis reactor), slurry pump (12), steam supply (13), pressure control valve (14), let down valve (15), flash tank (16), sample port (17), receiving tanks (18), and condenser (19).

In certain embodiments, said mixture is substantially free of $C_1$-$C_5$ alcohol.

In certain embodiments, said starting lignocellulosic biomass is in the form of logs.

In certain embodiments, said starting lignocellulosic biomass is substantially free of acid functionality. Acid functionalities include the acetyl group. Acid functionalities present in biomass may be measured by solids analysis—an analytical procedure where all of the C—O—C bonds are broken in the presence of strong acid (e.g., sulfuric acid), and then the resulting liquid is analyzed using high performance liquid chromatography (HPLC), which shows the amount of acid (e.g., acetyl) groups on the biomass.

In certain embodiments, said starting lignocellulosic biomass is substantially stable to autohydrolysis. As used herein, "autohydrolysis" is a process in which acid groups naturally present on biomass are released from the biomass during a hydrothermal treatment (e.g., elevated temperature and/or pressure in a liquid comprising water). The acid functionalities released during hydrothermal treatment lower the pH of the biomass/liquid mixture, causing at least a portion of the polysaccharides (such as hemicellulose) present in the biomass to hydrolyze (i.e., autohydrolyze). As used herein, "substantially stable to autohydrolysis" means (a) biomass that does not have sufficient acid functionalities to enable at least partial (e.g., substantial or complete) autohydrolysis to occur during hydrothermal treatment, and/or (b) biomass that has sufficient acid functionalities with the potential for autohydrolysis to occur, but, as a consequence of the structural and/or chemical characteristics of the biomass, the acid functionalities are not released in sufficient quantity for at least partial autohydrolysis to occur and/or the released acid functionalities are unable to facilitate at least partial (e.g., substantial or complete) autohydrolysis of the biomass.

In certain embodiments, said lignocellulosic biomass is derived from hardwood, softwood, agricultural residue, grass, algae, paper, waste lignocellulosic biomass, thermally processed cellulosic biomass, chemically processed cellulosic biomass, or combinations thereof.

In certain embodiments, said lignocellulosic biomass has a particle size less than about 500 µm, e.g., less than about 450 µm, less than about 400 µm, less than about 350 µm, less than about 300 µm, less than about 250 µm, less than about 200 µm, less than about 150 µm, less than about 125 µm, less than about 100 µm, less than about 75 µm, less than about 50 µm, or less than about 25 µm. Alternatively, said lignocellulosic biomass has a particle size larger than about 5 µm, e.g., larger than about 10 µm, larger than about 25 µm, larger than about 50 µm, larger than about 75 µm, larger than about 100 µm, larger than about 125 µm, larger than about 150 µm, larger than about 200 µm, larger than about 250 µm, larger than about 300 µm, larger than about 350 µm, larger than about 400 µm, or larger than about 450 µm. Thus, the particle size of said lignocellulosic biomass can be bounded by any two of the foregoing endpoints. For example, the particle size can be about 250 µm to about 450 µm, about 25 µm to about 125 µm, or about 400 µm to about 500 µm.

In certain embodiments, said $C_5$ or $C_6$ saccharide is at least one sugar selected from the group consisting of $C_5$ monosaccharide, $C_5$ oligosaccharide having a degree of polymerization less than about 15, $C_6$ monosaccharide, $C_6$ oligosaccharide having a degree of polymerization less than about 15, and combinations thereof.

In certain embodiments, said $C_5$ or $C_6$ saccharide is said $C_5$ monosaccharide, and said $C_5$ monosaccharide is at least one sugar selected from the group consisting of xylose, arabinose, lyxose, ribose, xylulose, and combinations thereof.

In certain embodiments, said $C_5$ or $C_6$ saccharide is said $C_6$ monosaccharide, and said $C_6$ monosaccharide is at least one sugar selected from the group consisting of glucose, mannose, galactose, fructose, and combinations thereof.

In certain embodiments, said $C_5$ or $C_6$ saccharide is said $C_5$ oligosaccharide, and said $C_5$ oligosaccharide has a degree of polymerization of about 2 to about 15. For example, the $C_5$ oligosaccharide has a degree of polymerization of about 2 or more, e.g., about 3 or more, about 4 or more, about 5 or more, about 6 or more, about 7 or more, about 8 or more, about 9 or more, about 10 or more, about 11 or more, about 12 or more, about 13 or more, or about 14 or more. Alternatively, or in addition, the $C_5$ oligosaccharide has a degree of polymerization of about 15 or less, e.g., about 14 or less, about 13 or less, about 12 or less, about 11 or less, about 10 or less, about 9 or less, about 8 or less, about 7 or less, about 6 or less, about 5 or less, about 4 or less, or about 3 or less. Thus, the $C_5$ oligosaccharide can have a degree of polymerization bounded by any two of the foregoing endpoints. For example, the $C_5$ oligosaccharide can have a degree of polymerization of about 4 to about 10, about 6 to about 12, or about 3 to about 5. In a preferred embodiment, the $C_5$ oligosaccharide has a degree of polymerization of about 2 to about 12.

In certain embodiments, said $C_5$ or $C_6$ saccharide is said $C_6$ oligosaccharide, and said $C_6$ oligosaccharide has a degree of polymerization of about 2 to about 15. For example, the $C_6$ oligosaccharide has a degree of polymerization of about 2 or more, e.g., about 3 or more, about 4 or more, about 5 or more, about 6 or more, about 7 or more, about 8 or more, about 9 or more, about 10 or more, about 11 or more, about 12 or more, about 13 or more, or about 14 or more. Alternatively, or in addition, the $C_6$ oligosaccharide has a degree of polymerization of about 15 or less, e.g., about 14 or less, about 13 or less, about 12 or less, about 11 or less, about 10 or less, about 9 or less, about 8 or less, about 7 or less, about 6 or less, about 5 or less, about 4 or less, or about 3 or less. Thus, the $C_6$ oligosaccharide can have a degree of polymerization bounded by any two of the foregoing endpoints. For example, the $C_6$ oligosaccharide can have a degree of polymerization of about 3 to about 9, about 10 to about 15, or about 2 to about 7. In a preferred embodiment, the $C_6$ oligosaccharide has a degree of polymerization of about 2 to about 14.

In certain embodiments, said $C_5$ or $C_6$ saccharide is a combination of glucose and xylose.

In certain embodiments, the method further comprises heating said mixture to a temperature of at least about 150° C. prior to said contacting step. For example, the mixture can be heated to a temperature of at least about 175° C., at least about 200° C., at least about 225° C., at least about 250° C., at least about 275° C., at least about 300° C., at least about 325° C., or at least about 350° C., prior to the contacting step. Alternatively, or in addition, the mixture can be heated to a temperature of about 360° C. or less, e.g., about 350° C. or less, about 325° C. or less, about 300° C. or less, about 275° C. or less, about 250° C. or less, about 225° C. or less, about 200° C. or less, or about 175° C. or less, prior to the contacting step. Thus, prior to the contacting step, the mixture can be heated to a temperature bounded by any two of the foregoing endpoints. For example, the mixture can be heated to a temperature of about 225° C. to about 350° C., about 275° C. to about 325° C., or about 175° C. to about 250° C., prior to the contacting step. In a preferred embodiment, the mixture is heated to a temperature of at least about 200° C. prior to the contacting step.

In certain embodiments, the solids content of the mixture, based on the total weight of the mixture, is about 1 wt. % or more, e.g., about 5 wt. % or more, about 10 wt. % or more, about 11 wt. % or more, about 12 wt. % or more, about 13 wt. % or more, about 14 wt. % or more, about 15 wt. % or more, about 16 wt. % or more, about 17 wt. % or more, about 18 wt. % or more, about 19 wt. % or more, about 20 wt. % or more, about 21 wt. % or more, about 22 wt. % or more, about 23 wt. % or more, about 24 wt. % or more, about 25 wt. % or more, about 26 wt. % or more, about 27 wt. % or more, about 28 wt. % or more, about 29 wt. % or more, about 30 wt. % or more, about 32 wt. % or more, or about 34 wt. % or more. Alternatively, or in addition, the solids content of the mixture, based on the total weight of the mixture, is about 35 wt. % or less, e.g., about 34 wt. % or less, about 32 wt. % or less, about 30 wt. % or less, about 29 wt. % or less, about 28 wt. % or less, about 27 wt. % or less, about 26 wt. % or less, about 25 wt. % or less, about 24 wt. % or less, about 23 wt. % or less, about 22 wt. % or less, about 21 wt. % or less, about 20 wt. % or less, about 19 wt. % or less, about 18 wt. % or less, about 17 wt. % or less, about 16 wt. % or less, about 15 wt. % or less, about 14 wt. % or less, about 13 wt. % or less, about 12 wt. % or less, about 11 wt. % or less, about 10 wt. % or less, about 5 wt. % or less. Thus, the solids content of the mixture can be bounded by any two of the foregoing endpoints. For example, the solids content of the mixture can be about 15 wt. % to about 29 wt. %, about 10 wt. % to about 18 wt. %, or about 24 wt. % to about 27 wt. %.

In certain embodiments, the method further comprises fermenting at least one of said $C_5$ and $C_6$ saccharide.

In certain embodiments, the method further comprises recovering at least one component released into a gas phase. In certain embodiments, said component is furfural, hydroxymethylfurfural, acetic acid, methanol, or a combination thereof.

The water that is contacted with the mixture has a temperature of at least about 374° C., e.g., at least about 375° C., at least about 380° C., at least about 390° C., at least about 400° C., at least about 410° C., at least about 420° C., at least about 430° C., at least about 440° C., at least about 450° C., at least about 460° C., at least about 470° C., at least about 480° C., at least about 490° C., at least about 500° C., at least about 510° C., at least about 520° C., at least about 530° C., at least about 540° C., or at least about 550° C. Alternatively, or in addition, the water that is contacted with the mixture has a temperature of about 575° C. or less, e.g., about 550° C. or less, about 540° C. or less, about 530° C. or less, about 520° C. or less, about 510° C. or less, about 500° C. or less, about 490° C. or less, about 480° C. or less, about 470° C. or less, about 460° C. or less, about 450° C. or less, about 440° C. or less, about 430° C. or less, about 420° C. or less, about 410° C. or less, about 400° C. or less, about 390° C. or less, about 380° C. or less, or about 375° C. or less. Thus, the water that is contacted with the mixture can have a temperature bounded by any two of the foregoing endpoints. For example, the water can have a temperature of about 374° C. to about 450° C., about 400° C. to about 520° C., or about 375° C. to about 430° C.

The water that is contacted with the mixture has a pressure of at least about 221 bar, e.g., at least about 225 bar, at least about 230 bar, at least about 250 bar, at least about 275 bar, at least about 300 bar, at least about 325 bar, at least about 350 bar, at least about 375 bar, at least about 400 bar, at least about 425 bar, at least about 450 bar, at least about 475 bar, at least about 500 bar, at least about 525 bar, at least about 550 bar, at least about 575 bar, at least about 600 bar, at least about 625 bar, at least about 650 bar, at least about 675 bar, at least about 700 bar, at least about 725 bar, at least about 750 bar, at least about 775 bar, or at least about 800 bar. Alternatively, or in addition, the water that is contacted with the mixture has a pressure of less than about 800 bar, e.g., less than about 775 bar, less than about 750 bar, less than about 725 bar, less than about 700 bar, less than about 675 bar, less than about 650 bar, less than about 625 bar, less than about 600 bar, less than about 575 bar, less than about 550 bar, less than about 525 bar, less than about 500 bar, less than about 475 bar, less than about 450 bar, less than about 425 bar, less than about 400 bar, less than about 375 bar, less than about 350 bar, less than about 325 bar, less than about 300 bar, less than about 275 bar, less than about 250 bar, or less than about 225 bar. Thus, the pressure of the water that is contacted with the mixture can be bounded by any two of the foregoing endpoints. For example, the pressure can be about 230 bar to about 500 bar, about 325 bar to about 750 bar, or about 275 bar to about 350 bar.

In certain embodiments, said duration is about 0.1 seconds to about 10 seconds. For example, the duration is about 0.1 seconds or more, e.g., about 0.2 seconds or more, about 0.3 seconds or more, about 0.4 seconds or more, about 0.5 seconds or more, about 0.6 seconds or more, about 0.7 seconds or more, about 0.8 seconds or more, about 0.9 seconds or more, about 1 seconds or more, about 1.1 seconds or more, about 1.2 seconds or more, about 1.3 seconds or more, about 1.4 seconds or more, about 1.5 seconds or more, about 2 seconds or more, about 2.5 seconds or more, about 3 seconds or more, about 3.5 seconds or more, about 4 seconds or more, about 4.5 seconds or more, about 5 seconds or more, about 6 seconds or more, about 7 seconds or more, about 8 seconds or more, or about 9 seconds or more. Alternatively, or in addition, the duration is about 10 seconds or less, e.g., about 9 seconds or less, about 8 seconds or less, about 7 seconds or less, about 6 seconds or less, about 5 seconds or less, about 4.5 seconds or less, about 4 seconds or less, about 3.5 seconds or less, about 3 seconds or less, about 2.5 seconds or less, about 2 seconds or less, about 1.5 seconds or less, about 1.4 seconds or less, about 1.3 seconds or less, about 1.2 seconds or less, about 1.1 seconds or less, about 1 seconds or less, about 0.9 seconds or less, about 0.8 seconds or less, about 0.7 seconds or less, about 0.6 seconds or less, about 0.5 seconds or less, about 0.4 seconds or less, about 0.3 seconds or less, or about 0.2 seconds or less. Thus, the duration can be bounded by any two of the foregoing endpoints. For example, the duration can be about 0.1 seconds to about 0.3 seconds, about 1.1 seconds to about 5 seconds, or about 0.9 seconds to about 9 seconds. In a preferred embodiment, the duration is about 1.4 seconds or less.

In certain embodiments, the method further comprises purifying at least one of said $C_5$ and $C_6$ saccharide. Suitable purification methods include chromatography and the like. Simulated moving bed chromatography is preferred.

The methods of the invention are preferably run continuously, although they may be run as batch or semi-batch processes.

The methods of the invention may be carried out in any suitable reactor, including, but not limited to, a tubular reactor, a digester (vertical, horizontal, or inclined), or the like. Suitable digesters include the digester system described in U.S. Pat. No. 8,057,639, which include a digester and a steam explosion unit, the entire disclosure of which is incorporated herein by reference.

In certain embodiments, the $C_5$ and $C_6$ saccharides sugars may be fermented to ethanol, butanol, and combinations thereof, using techniques known to those skilled in the art, including, but not limited to, yeast fermentations using *Saccharomyces cerevisiae* and *Clostridium* sp. In certain preferred embodiments, an oligomer fermentor is able to uptake oligomers directly (generally up to a maximum size, for example, of 6 mer units, for *Clostridium thermocellum*).

In certain embodiments, the yield of said $C_5$ or $C_6$ saccharides is at least 30% of theoretical yield, e.g., at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of theoretical yield. In a preferred embodiment, the yield of the $C_5$ and $C_6$ saccharides is at least about 70% of theoretical yield, most preferably at least about 85% of theoretical yield. The percent yield, as used herein, may refer to the percent yield of $C_5$ saccharides only, $C_6$ saccharides only, or a combination of $C_5$ and $C_6$ saccharides. The percent yield, as used herein, may also refer to the percent yield of any of the specific $C_5$ and/or $C_6$ saccharides, as defined elsewhere herein.

In certain embodiments, the conversion of said $C_5$ and/or $C_6$ saccharides is at least about 20%, e.g., at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%. The conversion, as used herein, may refer to the conversion of $C_5$ saccharides only, $C_6$ saccharides only, or a combination of $C_5$ and $C_6$ saccharides. The conversion, as used herein, may also refer to the conversion of any of the specific $C_5$ and/or $C_6$ saccharides, as defined elsewhere herein. In a preferred embodiment, the conversion of $C_6$ saccharides is at least about 50%. In a preferred embodiment, the conversion of $C_5$ saccharides is at least about 85%.

In another embodiment, the invention is directed to products produced by the methods described herein.

In other embodiments, the invention is directed to compositions, comprising:
about 0.1% by weight to about 4% by weight, based on the total weight of the composition, of $C_5$ monosaccharide;
about 0.1% by weight to about 4% by weight, based on the total weight of the composition, of $C_5$ oligosaccharide having a degree of polymerization less than about 15;
about 0.1% by weight to about 8% by weight, based on the total weight of the composition, of $C_6$ monosaccharide; and
about 0.1% by weight to about 8% by weight, based on the total weight of the composition, of $C_6$ oligosaccharide having a degree of polymerization less than about 15.

In other embodiments, the invention is directed to compositions, comprising:
about 0.1% by weight to about 4% by weight, based on the total weight of the composition, of $C_5$ monosaccharide; and
about 0.1% by weight to about 8% by weight, based on the total weight of the composition, of $C_6$ monosaccharide.

The $C_5$ monosaccharide can be present in a composition in an amount of at least about 0.1%, e.g., at least about 0.5%, at least about 1%, at least about 1.5%, at least about 2%, at least about 2.5%, at least about 3%, or at least about 3.5%, by weight, based on the total weight of the composition. Alternatively, or in addition, the $C_5$ monosaccharide can be present in a composition in an amount of less than about 4%, e.g., less than about 3.5%, less than about 3%, less than about 2.5%, less than about 2%, less than about 1.5%, less than about 1%, or less than about 0.5%, by weight, based on the total weight of the composition. Thus, the amount of $C_5$ monosaccharide present in a composition can be bounded by any two of the foregoing endpoints. For example, the $C_5$ monosaccharide can be present in a composition in an amount of about 0.5% to about 3.5%, about 1% to about 4%, or about 2.5% to about 3%, by weight, based on the total weight of the composition.

The $C_5$ oligosaccharide can be present in a composition in an amount of at least about 0.1%, e.g., at least about 0.5%, at least about 1%, at least about 1.5%, at least about 2%, at least about 2.5%, at least about 3%, or at least about 3.5%, by weight, based on the total weight of the composition. Alternatively, or in addition, the $C_5$ oligosaccharide can be present in a composition in an amount of less than about 4%, e.g., less than about 3.5%, less than about 3%, less than about 2.5%, less than about 2%, less than about 1.5%, less than about 1%, or less than about 0.5%, by weight, based on the total weight of the composition. Thus, the amount of $C_5$ oligosaccharide present in a composition can be bounded by any two of the foregoing endpoints. For example, the $C_5$ oligosaccharide can be present in a composition in an amount of about 1.5% to about 4.5%, about 0.1% to about 2%, or about 1.5% to about 3.5%, by weight, based on the total weight of the composition.

The $C_6$ monosaccharide can be present in a composition in an amount of at least about 0.1%, e.g., at least about 0.5%, at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, or at least about 7.5%, by weight, based on the total weight of the composition. Alternatively, or in addition, the $C_6$ monosaccharide can be present in a composition in an amount of less than about 8%, e.g., less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, or less than about 0.5%, by weight, based on the total weight of the composition. Thus, the amount of $C_6$ monosaccharide present in a composition can be bounded by any two of the foregoing endpoints. For example, the $C_6$ monosaccharide can be present in a composition in an amount of about 0.5% to about 6.5%, about 1.5% to about 7%, or about 2.5% to about 3%, by weight, based on the total weight of the composition.

The $C_6$ oligosaccharide can be present in a composition in an amount of at least about 0.1%, e.g., at least about 0.5%, at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, or at least about 7.5%, by weight, based on the total weight of the composition. Alternatively, or in addition, the $C_6$ oligosaccharide can be present in a composition in an amount of less than about 8%, e.g., less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, or less than about 0.5%, by weight, based on the total weight of the composition. Thus, the amount of $C_6$ oligosaccharide present in a composition can be bounded by any two of the foregoing endpoints. For example, the $C_6$ oligosaccharide can be present in a composition in an amount of about 0.5% to about 6.5%, about 1.5% to about 7%, or about 2.5% to about 3%, by weight, based on the total weight of the composition.

In certain embodiments, said compositions described herein, further comprise less than about 15%, preferably less than about 10%, by weight, based on the total weight of the composition, of byproducts, wherein said byproducts are selected from the group consisting of glycolaldehyde, glycolic acid, glyceraldehyde, and combinations thereof.

The compositions of the invention are particularly useful as starting materials that may be fermented into ethanol or butanol, or converted into other useful materials.

Glycolaldehyde may be easily hydrogenated to mono-ethylene glycol (MEG), using RANEY nickel catalyst, for example. RANEY nickel catalyst is a fine-grained solid composed mostly of nickel derived from a nickel-aluminum alloy. RANEY nickel is also known in the chemical arts as "skeletal catalyst" or "sponge-metal catalyst." In addition, glycolic acid, glycerolaldehyde, lactic acid, and acetic acid are generated, which may be isolated using, for example, liquid-liquid extraction.

The products and compositions produced by the methods of the invention may be utilized in a wide variety of applications, where $C_5$ and $C_6$ sugars are conventionally utilized, including, but not limited to, the production of various chemicals and fuels using fermentative, enzymatic, catalytic, and non-catalytic (e.g., thermal decomposition) processes. Such processes are useful for preparing feedstocks for the preparation of the following non-exhaustive list:

fuels (such as gasoline, jet fuel, butanol, and the like);
chemicals (such as acetic acid, acetic anhydride, acetone, acrylic acid, adipic acid, benzene, ethanol, ethylene, ethylene glycol, ethylene oxide, methanol, polypropylene, terephthalic acid, toluene, xylene, 1,3-propanediol, 1,4-butanediol, and the like);
pharmaceuticals and foods (such as acetoin, alanine, arabitol, ascorbic acid, aspartic acid, citric acid, coumaric acid, fumaric acid, glycerol, glycine, kojic acid, lactic acid, lysine, malonic acid, proline, propionic acid, serine, sorbitol, succinic acid, threonine, xylitol, sugar acids (glucaric acid, gluconic acid, xylonic acids), and the like);
specialty chemicals (such as acontic acid, glutamic acid, malic acid, oxalic acid, and the like);
textile applications (such as formic acid and the like); and
industrial intermediates (acetaldehyde, 3-hydroxypropionic acid, 2,5-furan dicarboxylic acid, furfural, glutaric acid, itaconic acid, levulinic acid, and the like).

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

A trial was run using hardwood flour biomass (140 mesh) in a water slurry (12% solids) as feedstock into the supercritical hydrolysis (SH) system shown in FIG. 1, set up for steam explosion by flashing. The system was set up with two let down valves (LDV). The second LDV was located immediately after the first LDV. Reactor length was 12 feet. No in-line mixers were located in the reactor or elsewhere in the system. The reactor had a six inch spool piece in the middle of the reactor that was removed following the run to measure the thickness of any fouling and record observations on the fouling.

The slurry was preheated to 200° C. and the supercritical water was heated to 400° C. before being mixed in the reactor. The reactor target temperature was 375° C. The target temperature after the quench mix was 280° C. The reactor pressure was set at 3335 psi. The second pressure was 2175 psi.

Approximately 100% of the xylan was converted, with xylose yields of 70-85%. Approximately 25-50% of the glucan was converted, with glucose yields of 25-30%. The fouling in the system was significantly less during the trial than it typically is using pretreated solids as feed in a two-stage process.

Example 2

A second trial was run using hardwood flour biomass (140 mesh) in a water slurry (4% solids) as feedstock into a supercritical hydrolysis (SH) system similar to that shown in FIG. 1. The residence time was about 1 sec. The system was set up with one LDV, and an in-line mixer was located in the reactor. The composition of the hardwood flour biomass is shown below in Table 1 (100 kg total mass basis).

A third trial was run using softwood flour (loblolly pine) biomass (140 mesh) in a water slurry (4% solids) as feedstock into a supercritical hydrolysis (SH) system similar to that shown in FIG. 1. The third trial was performed in duplicate at two different residence times (about 1 sec and about 2 sec), and the two experiments for each residence time were averaged to obtain the values reported herein. The system was set up with one LDV, and an in-line mixer was located in the reactor. The composition of the softwood flour biomass is shown below in Table 1 (100 kg total mass basis).

TABLE 1

| Component | Hardwood (kg) | Softwood (kg) |
| --- | --- | --- |
| Glucan | 41.41 | 39 |
| Xylan | 17.42 | 8.7 |
| Arabinan | 0.85 | 1.3 |
| Galactan | 0.89 | 2.1 |
| Mannan | 2.12 | 7.8 |
| Acetyl | 3.2 | 1 |

In both the second and third trials, the slurry was preheated to about 220° C. before being contacted in the reactor with supercritical water having a temperature of about 400° C. The reactor target temperature was about 364° C. to about 383° C. The "residence time" is the length of time the biomass resides within the reactor during the trial. The target temperature after the quench mix was about 200° C. The reactor pressure was set at about 3500 psi. Table 2 shows the compositions of the resulting liquor and solids after the softwood and hardwood feedstocks were subjected to single stage supercritical hydrolysis.

TABLE 2

|   |   |   | Softwood | |
| --- | --- | --- | --- | --- |
|   |   | Hardwood Residence Time about 1 sec | Residence Time about 1 sec | Residence Time about 2 sec |
|   | Component | Mass (kg) | Mass (kg) | Mass (kg) |
| Liquor | Glucose | 17.6 | 18 | 11.6 |
|   | Xylose | 11.6 | 3.75 | 2.49 |
|   | Arabinose | 0.14 | 0.139 | 0.146 |
|   | Galactose | 0.3 | 0.742 | 0.503 |
|   | Mannose | 1.24 | 5.46 | 3.37 |
| Solids | Glucan | 10.6 | 12 | 6.39 |
|   | Xylan | 0.35 | 0.2 | 0.105 |
|   | Arabinan | 0.03 | 0.056 | 0.02 |
|   | Galactan | 0.03 | 0.125 | 0.066 |
|   | Mannan | 0.11 | 0.48 | 0.255 |

Table 3 shows the percent yields of monomeric sugars in the resulting liquor after supercritical hydrolysis. The percent yield is calculated by dividing the amount of a specific sugar (e.g., glucose) present in the liquor after subjecting the biomass to supercritical hydrolysis by the maximum amount of the specific sugar (e.g., glucose) that could have possibly been formed (i.e., the theoretical maximum amount of a specific sugar that could have been formed based on the starting composition of the biomass).

TABLE 3

| Component | Hardwood Yield (%) | Softwood Residence Time about 1 sec Yield (%) | Softwood Resident Time about 2 sec Yield (%) |
|---|---|---|---|
| Glucose | 38 | 41 | 26 |
| Xylose | 59 | 38 | 25 |
| Arabinose | 14 | 9.4 | 9.9 |
| Galactose | 30 | 32 | 22 |
| Mannose | 53 | 63 | 39 |

Table 4 shows the percent conversions (to other products) of the polysaccharides in the starting biomass after being subjected to supercritical hydrolysis. The percent conversion is calculated by subtracting the amount of a specific polysaccharide (e.g., glucan) remaining after supercritical hydrolysis from the amount of the specific polysaccharide (e.g., glucan) in the starting composition, and dividing the result by the amount of the specific polysaccharide (e.g., glucan) in the starting composition.

TABLE 4

| Component | Hardwood Conversion (%) | Softwood Residence Time about 1 sec Conversion (%) | Softwood Resident Time about 2 sec Conversion (%) |
|---|---|---|---|
| Glucan | 74 | 69 | 84 |
| Xylan | 98 | 98 | 99 |
| Arabinan | 96 | 96 | 98 |
| Galactan | 97 | 94 | 97 |
| Mannan | 95 | 94 | 97 |

Figure 2A:
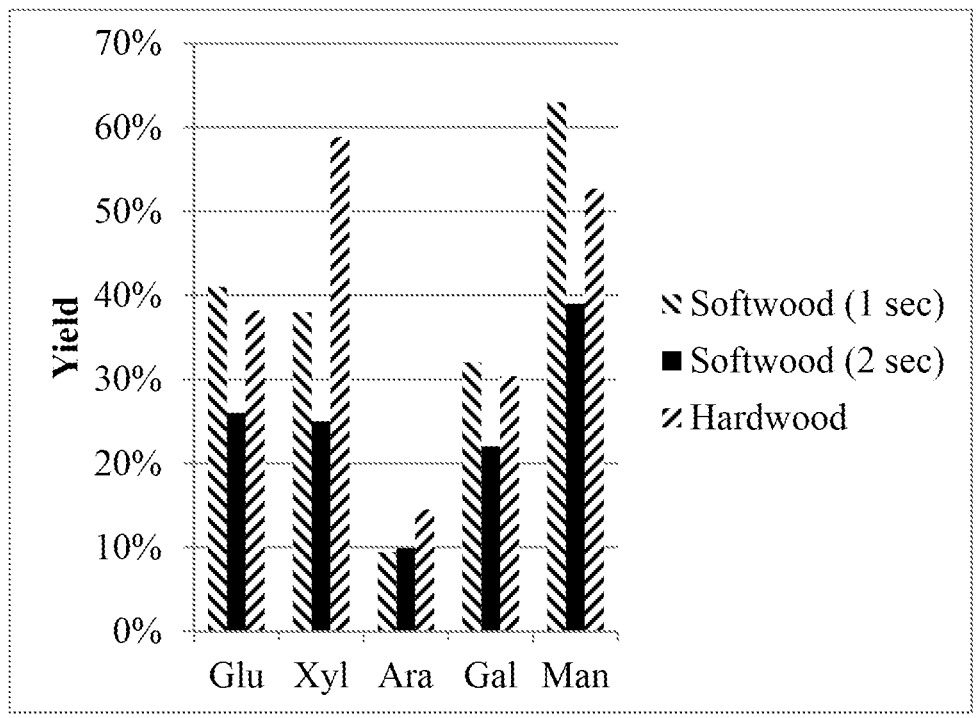
FIG. 2A illustrates percent yields of different sugars obtained when subjecting hardwood or softwood to methods of the invention.
Figure 2B:
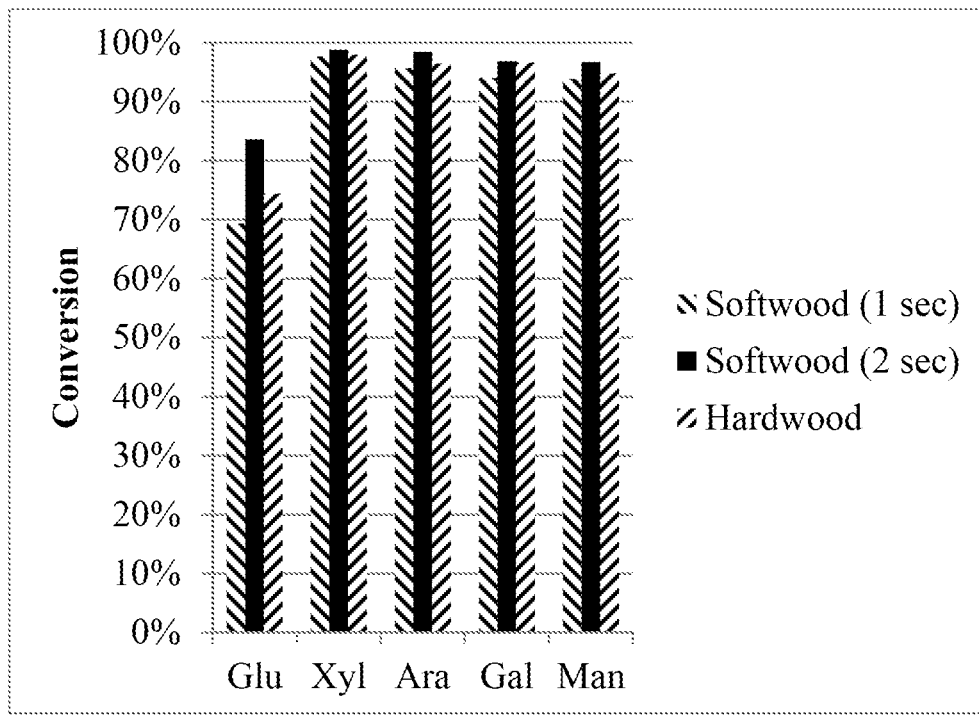
FIG. 2B illustrates percent conversion of different polysaccharides present in hardwood or softwood when these feedstocks are subjected to methods of the invention.

FIG. 2A shows the percent yield of glucose, xylose, arabinose, galactose, and mannose for the second and third trials for hardwood and softwood (at two different residence times), respectively. FIG. 2B shows the percent conversion of glucan, xylan, arabinan, galactan, and mannan for the second and third trials for hardwood and softwood (at two different residence times), respectively. As shown in FIGS. 2A and 2B, approximately 90-100%% of the xylan was converted for both hardwood and softwood, with xylose yields of about 20-60%. If the softwood data for a 2 sec residence time is excluded, the xylose yields are nearly 40-60%. Approximately 70-85% of the glucan was converted, with glucose yields of about 25-40%. Again, if the softwood data for a 2 sec residence time is excluded, the glucose yields are nearly 40%. It is apparent that the process may be further optimized to further improve the yields of sugars.

While the preferred forms of the invention have been disclosed, it will be apparent to those skilled in the art that various changes and modifications may be made that will achieve some of the advantages of the invention without departing from the spirit and scope of the invention. Therefore, the scope of the invention is to be determined solely by the claims to be appended.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method, comprising:
   size reducing a starting lignocellulosic biomass to form a lignocellulosic biomass having a particle size less than about 500 μm;
   forming a mixture comprising:
      water; and
      said lignocellulosic biomass having a particle size less than about 500 μm; and
   contacting water at a temperature of at least about 374° C. and a pressure of at least about 221 bar with said mixture for a duration sufficient to produce at least one $C_5$ or $C_6$ saccharide;
   wherein said mixture is substantially free of exogenous acid.

2. The method of claim 1, wherein said size reducing comprises steam exploding said starting lignocellulosic biomass optionally in the presence of a chemical selected from the group consisting of ammonia, sulfur dioxide, and combinations thereof.

3. The method of claim 1, wherein said size reducing comprises comminuting said starting lignocellulosic biomass.

4. The method of claim 1, wherein said mixture is substantially free of $C_1$-$C_5$ alcohol.

5. The method of claim 1, wherein said starting lignocellulosic biomass is in the form of logs.

6. The method of claim 1, wherein said starting lignocellulosic biomass is substantially free of acid functionality.

7. The method of claim 1, wherein said starting lignocellulosic biomass is substantially stable to autohydrolysis.

8. The method of claim 1, wherein said lignocellulosic biomass is derived from hardwood, softwood, agricultural residue, grass, algae, paper, waste lignocellulosic biomass, thermally processed cellulosic biomass, chemically processed cellulosic biomass, or combinations thereof.

9. The method of claim 1, wherein said lignocellulosic biomass has a particle size less than about 250 μm.

10. The method of claim 1, wherein said lignocellulosic biomass has a panicle size less than about 125 μm.

11. The method of claim 1, wherein said lignocellulosic biomass has a particle size less than about 25 μm.

12. The method of claim 1, wherein said $C_5$ or $C_6$ saccharide is at least one sugar selected from the group consisting of $C_5$ monosaccharide, $C_5$ oligosaccharide having a degree of polymerization less than about 15, $C_6$ monosaccharide, $C_6$ oligosaccharide having a degree of polymerization less than about 15, and combinations thereof.

13. The method of claim 12, wherein said $C_5$ or $C_6$ saccharide is said $C_5$ monosaccharide, and said $C_5$ monosaccharide is at least one sugar selected from the group consisting of xylose, arabinose, lyxose, ribose, xylulose, and combinations thereof.

14. The method of claim 12,
wherein said $C_5$ or $C_6$ saccharide is said $C_6$ monosaccharide, and said $C_6$ monosaccharide is at least one sugar selected from the group consisting of glucose, mannose, galactose, fructose, and combinations thereof.

15. The method of claim 12,
wherein said $C_5$ or $C_6$ saccharide is said $C_5$ oligosaccharide, and said $C_5$ oligosaccharide has a degree of polymerization of about 2 to about 12.

16. The method of claim 12,
wherein said $C_5$ or $C_6$ saccharide is said $C_6$ oligosaccharide, and said $C_6$ oligosaccharide has a degree of polymerization of about 2 to about 14.

17. The method of claim 1,
wherein said $C_5$ or $C_6$ saccharide is a combination of glucose and xylose.

18. The method of claim 1, further comprising:
heating said mixture to a temperature of at least about 200° C. subsequent to said size reducing step and prior to said contacting step.

19. The method of claim 1, further comprising:
fermenting at least one of said $C_5$ and $C_6$ saccharide.

20. The method of claim 1, further comprising;
recovering at least one component released into a gas phase.

21. The method of claim 20,
wherein said component is furfural, hydroxymethylfurfural, acetic acid, methanol, or a combination thereof.

22. The method of claim 1,
wherein said duration is about 0.1 seconds to about 10 seconds.

23. The method of claim 1, further comprising:
purifying at least one of said $C_5$ and $C_6$ saccharide.

24. The method of claim 23,
wherein said purifying comprises simulated moving bed chromatography.

25. A composition produced by the method of claim 1.

26. A composition, comprising:
about 0.1% by weight to about 4% by weight, based on the total weight of the composition, of $C_5$ monosaccharide;
about 0.1% by weight to about 4% by weight, based on the total weight of the composition, of $C_5$ oligosaccharide having a degree of polymerization less than about 15;
about 0.1% by weight to about 8% by weight, based on the total weight of the composition, of $C_6$ monosaccharide; and
about 0.1% by weight to about 8% by weight, based on the total weight of the composition, of $C_6$ oligosaccharide having a degree of polymerization less than about 15.

27. A composition, comprising:
about 0.1% by weight to about 4% by weight, based on the total weight of the composition, of $C_5$ monosaccharide; and
about 0.1% by weight to about 8% by weight, based on the total weight of the composition, of $C_6$ monosaccharide.

* * * * *